United States Patent
Törnsten

(10) Patent No.: US 10,166,346 B2
(45) Date of Patent: Jan. 1, 2019

(54) BRUISELESS CANNULA

(71) Applicant: Q-Med AB, Uppsala (SE)

(72) Inventor: Jonas Törnsten, Uppsala (SE)

(73) Assignee: Q-MED AB, Uppsala (SE)

( * ) Notice: Subject to any disclaimer, the term of this patent is extended or adjusted under 35 U.S.C. 154(b) by 466 days.

(21) Appl. No.: 14/369,916

(22) PCT Filed: Dec. 19, 2012

(86) PCT No.: PCT/EP2012/076200
§ 371 (c)(1),
(2) Date: Jun. 30, 2014

(87) PCT Pub. No.: WO2013/098166
PCT Pub. Date: Jul. 4, 2013

(65) Prior Publication Data
US 2015/0018798 A1 Jan. 15, 2015

(30) Foreign Application Priority Data

Dec. 30, 2011 (EP) .................................. 11196145

(51) Int. Cl.
*A61M 5/32* (2006.01)
*A61M 5/46* (2006.01)
*A61M 5/34* (2006.01)

(52) U.S. Cl.
CPC .......... *A61M 5/3287* (2013.01); *A61M 5/329* (2013.01); *A61M 5/3286* (2013.01);
(Continued)

(58) Field of Classification Search
CPC .... A61M 5/3287; A61M 5/347; A61M 5/329; A61M 5/3286; A61M 5/46; A61M 2005/3267
See application file for complete search history.

(56) References Cited

U.S. PATENT DOCUMENTS

| | | | |
|---|---|---|---|
| 1,527,291 A * | 2/1925 | Zorraquin | A61M 5/32 604/158 |
| 3,530,492 A * | 9/1970 | Ferber | A61M 5/32 604/117 |

(Continued)

FOREIGN PATENT DOCUMENTS

| | | |
|---|---|---|
| GB | 624269 A | 6/1949 |
| JP | H-04501672 A | 3/1992 |

(Continued)

OTHER PUBLICATIONS

International Search Report (PCT/ISA/210) dated May 8, 2013, by the European Patent Office as the International Searching Authority for International Application No. PCT/EP2012/076200.

(Continued)

*Primary Examiner* — Bhisma Mehta
*Assistant Examiner* — Jenna Zhang
(74) *Attorney, Agent, or Firm* — Buchanan, Ingersoll & Rooney P.C.

(57) ABSTRACT

A needle device including a housing. The housing includes a first housing element provided towards a proximal end of said needle device and a second housing element provided towards a distal end of said needle device. A cutting element having a sharp proximal end is arranged at a proximal end of said first housing element. A cannula having a blunt proximal end is fitted to the second housing element and an opening for the cannula is provided at the proximal end of the first housing element. The first housing element and the second housing element are moveable relative to each other between an extended position where the proximal end of the cannula does not extend beyond the proximal end of the cutting element and a compressed position where the cannula extends through the opening of the first housing element and past the proximal end of the cutting element.

14 Claims, 5 Drawing Sheets

(52) U.S. Cl.
CPC .............. *A61M 5/347* (2013.01); *A61M 5/46* (2013.01); *A61M 2005/3267* (2013.01)

(56) References Cited

U.S. PATENT DOCUMENTS

| | | | | |
|---|---|---|---|---|
| 3,840,008 | A * | 10/1974 | Noiles | A61M 5/3286 604/117 |
| 4,345,589 | A * | 8/1982 | Hiltebrandt | A61B 1/00105 348/E5.047 |
| 5,098,388 | A * | 3/1992 | Kulkashi | A61B 17/3496 604/158 |
| 5,098,389 | A * | 3/1992 | Cappucci | A61M 5/3286 604/158 |
| 5,104,381 | A * | 4/1992 | Gresl | A61B 1/00135 604/158 |
| 5,139,485 | A * | 8/1992 | Smith | A61B 17/3496 604/158 |
| 5,472,430 | A * | 12/1995 | Vaillancourt | A61M 5/326 600/576 |
| 5,685,852 | A * | 11/1997 | Turkel | A61B 17/3401 604/159 |
| 6,077,244 | A * | 6/2000 | Botich | A61M 25/0606 604/110 |
| 6,537,253 | B1 * | 3/2003 | Haindl | A61M 25/0631 604/158 |
| 6,776,776 | B2 * | 8/2004 | Alchas | A61M 5/3129 604/117 |
| 7,217,275 | B2 * | 5/2007 | Crabtree | A61B 17/3403 604/506 |
| 2011/0282271 | A1 * | 11/2011 | Klein | A61M 5/158 604/22 |

FOREIGN PATENT DOCUMENTS

| | | |
|---|---|---|
| WO | 90/03815 A1 | 4/1990 |
| WO | WO 2004/067068 A1 | 8/2004 |
| WO | WO 2005/044116 A2 | 5/2005 |

OTHER PUBLICATIONS

Office Action (Notice of Acceptance) dated Apr. 15, 2015, by the Australian Patent Office in corresponding Australian Patent Application No. 2012361066. (2 pages).

Office Action (Notice of Reasons for Rejection) dated Sep. 27, 2016, by the Japanese Patent Office in Japanese Patent Application No. 2014-549427, English Translation of the Office Action. (4 pages).

* cited by examiner

BRUISELESS CANNULA

FIELD OF THE INVENTION

The present invention relates to a needle device for an injection apparatus for delivering liquid or gel compositions, such as viscous gels of, e.g., hyaluronic acid. It also relates to an injection apparatus using such needle device, the use of such needle device or injection apparatus and a method for administration of a liquid or gel composition.

BACKGROUND OF THE INVENTION

In certain fields of application, large numbers of injections have to be made within a region of skin of a patient. One example of such field of application is cosmetic treatment where e.g. dermal fillers in the form of gels of hyaluronic acid are injected into the tissue of a patient in order to fill out undesirable wrinkles and similar. In the prior art, injection is typically done by using a syringe fitted with a hypodermic needle having a sharp, beveled tip. One challenge during such injection is to avoid bruising of the skin tissue or tissue trauma. This is especially relevant when visible skin regions such as the face, hands or décolletage of a patient is treated. Another drawback with the use of a traditional syringe in that type of treatment is that it can be time consuming considering the large number of injections sometimes required. In another prior art method, a number of incisions are made over a surface to be treated with a first instrument, e.g. a scalpel or a sharp hypodermic needle. Then, in a following stage, a blunt cannula is introduced through these openings and a liquid or gel composition is injected. That prior art method does however involve a number of drawbacks. It is inexpedient and inconvenient to have to use two different instruments during the work and if a large number of injections are necessary, that method is very time consuming. Further, the risk of cutting too deep in the first stage is rather high which increases the risk of post-treatment bruising and tissue trauma. Another non-negligible disadvantage with that method is the fact that it can be quite hard to find the incisions when the blunt cannula is to be inserted since the opening is rather small. Prior art document U.S. Pat. No. 5,098,389 discloses a needle assembly having a handle with a short introducer needle mounted to the handle, and a blunt cannula mounted within the handle and slidable within the handle. The needle assembly is held at the handle with one hand, and pushed against the skin. The introducer needle thereby cuts an incision. Then the cannula is inserted with the other hand. Such a two-hand operation is undesirable. Additionally, the needle assembly is not constructed for multiple injections. Prior art document U.S. Pat. No. 3,840,008 discloses a needle having a pointed hollow piercing member slidably mounted about a blunt cannula. The piercing member has a collapsible bar, which is finger operated. After having introduced the piercing member while holding the finger on the bar, the user removes the finger and inserts the cannula. During the last mentioned part of the operation the bar collapses. The needle is difficult to use and is not constructed for multiple injections. Another example is disclosed in GB 624269, where an injection needle has an outer sharp needle and an inner blunt cannula. The injection needle is a typical single injection device.

SUMMARY OF THE INVENTION

It is an object of the present invention to reduce or eliminate the above mentioned and other drawbacks. This object and other objects are achieved by a needle device according to the present invention as defined in the appended claims. This object and other objects are also achieved by an injection apparatus as defined in the appended claims. Preferred embodiments of the present invention are defined in the dependent claims.

Thus, in accordance with an aspect of the present invention there is provided a needle device for an injection apparatus, wherein said needle device comprises a housing which can be mounted to an injection device, said housing comprising a first housing element provided towards a proximal end of said needle device and a second housing element provided towards a distal end of said needle device. A cutting element having a sharp proximal end is arranged at a proximal end of said first housing element. A cannula having a blunt proximal end is fitted to the second housing element and an opening for said cannula is provided at the proximal end of the first housing element. The first housing element and the second housing element are moveable relative to each other between an extended position and a compressed position where the proximal end of the cannula does not extend beyond the proximal end of the cutting element when the first and second housing elements are in the extended position and wherein the cannula extends through the opening of the first housing element and past the proximal end of the cutting element when the first and second housing elements are in the compressed position. This arrangement entails a number of advantages, the avoiding of bruising of the skin being one. Since the cutting element only is required for the initial creating of an opening in the skin and not for the injection itself, it's length can be reduced to only reach through the uppermost layer of the skin, the epidermis. In comparison with other skin layers, such as the dermis, the epidermis is rather tough and leathery and forms the outermost layer of the skin acting as a waterproof protective wrap over the body. The thickness of the epidermis varies over different regions of the body, between approximately 0.05 mm on the eyelids to approximately 1.5 mm on the palms and soles. The epidermis contains no blood vessels but is instead nourished by diffusion from blood capillaries extending to the upper layers of the underlying dermis. The absence of blood vessels in the epidermis means that bruising of the skin does not occur in this layer but rather in subjacent skin layers containing blood vessels. As soon as an opening is created in the epidermis the continued penetration into deeper skin layers is done with the blunt cannula while the cutting element remains in the epidermis penetrating position. The blunt cannula can penetrate through the underlying dermis and subcutis without performing any cutting of the tissue. Instead, the tissue is pushed aside as the blunt cannula penetrates it and the blood vessels can remain intact. As soon as the blunt cannula has reached the anticipated depth, injection of the liquid or gel composition can be performed. This collaboration between the cutting element and the blunt cannula ensures an easily worked device with which skin bruising and tissue trauma can be substantially avoided.

Furthermore, a resilient member is provided within the housing and arranged to bias the first housing element and the second housing element towards the extended position. The biasing force of the spring can be chosen to substantially correspond to the force necessary for the cutting element to penetrate the epidermis. A user then only has to force the needle device against a desirable skin region and the cutting element will penetrate the skin and the cannula will penetrate deeper to the desirable depth in one continuous motion.

In accordance with an embodiment of the injection device of the invention, the second housing element comprises an adaptor arranged to mount the needle device to an injection device and wherein said cannula is fitted to said adaptor and said adaptor being adjustably mounted to the second housing element such that it is possible to adjust how far beyond the proximal end of the cutting element the cannula extends when the first and the second housing elements are in the compressed position. By adjusting the relative position between the adaptor, and thus the cannula, and the second housing element, it is possible to adjust how deep the cannula penetrates into the tissue.

In accordance with an embodiment of the injection device of the invention, the adaptor is mounted to the second housing element by a threaded connection. A threaded connection provides for a simple, reliable and finely adjustable connection.

In accordance with an embodiment of the injection device of the invention, the cutting element comprises a beveled needle provided with a sharp tip, wherein the cannula and the beveled needle are coaxially mounted such that the cannula extends through the interior of the beveled needle when the first housing element is in the compressed position. The use of a beveled needle provides for a simple and cost effective solution. The beveled needle is mounted within the opening of the first housing element such that the blunt cannula can pass through its opening.

In accordance with an embodiment of the injection device of the invention, the cutting element extends partly around a perimeter of the opening in the first housing element. By providing the cutting element adjacent the opening of the first housing element but extending only around a part of the perimeter of said opening, the problem of coring can be avoided. Coring is a designation of the hole cutout of the skin that may occur when a hollow needle is used as a cutting element. This is highly undesirable as it will have a negative impact in appearance. If coring occurs, there is a risk that the cut out skin piece will be pushed into and left within the skin of the patient. By using a cutting element which extends only partly around a perimeter of the opening, an opening can be created which is more or less c-shaped, or even I-shaped, which is more favorable. Generally, the smaller the opening in the skin, the better since this will favour the healing process and lessens the risk of bruising and other post-treatment problems. However, the opening of course has to be large enough to allow the blunt cannula to enter.

In accordance with an embodiment of the injection device of the invention, the cutting element comprises a micro needle. Micro needles can for example be produced by silicon etching or micro molding and can be made extremely sharp producing a very clean incision which is favourable from a healing point of view.

In accordance with an embodiment of the injection device of the invention, the cannula having a blunt proximal end comprises a lateral orifice through which a liquid or gel composition can be delivered. The needle can be made of polished surgical steel and the lateral opening has a smooth design to avoid damage to the tissue while allowing the liquid or gel composition to flow easily through and out of the cannula.

In accordance with an embodiment of the injection device of the invention, the cutting element has a length between 0.05 mm to 1.5 mm. By using a cutting element with a length specifically adapted to the thickness of the epidermis of the designated skin area, the risk of skin bruising or tissue trauma can be even further reduced.

In accordance with another aspect of the invention, an injection apparatus is provided comprising an injector and a needle device as defined above.

In accordance with an embodiment of the injection apparatus of the invention, the injector comprises a container filled with a liquid or gel composition for cosmetic treatment.

In accordance with another aspect of the invention it is described the use of a needle device or an injection apparatus for avoiding bruising during percutaneous administration of a liquid or gel composition.

In accordance with an embodiment of the use of a needle device, the liquid or gel composition is for cosmetic treatment.

In accordance with another aspect of the invention a method for percutaneous administration of a liquid or gel composition is disclosed, said method comprising the following steps:
  penetrating the epidermis at a desirable skin region by pressing a cutting element having a sharp proximal end against the skin to create an opening in the epidermis;
  inserting a cannula having a blunt proximal end through the opening created in the epidermis by moving the cannula relative to the cutting element, while maintaining the cutting element in an epidermis-penetrating position;
  wherein the proximal end of the cannula is inserted to a greater depth in the skin than the proximal end of the cutting element; and
  administrating the liquid or gel composition through the cannula.

In accordance with an embodiment of the method for percutaneous administration of a liquid or gel composition of the invention, the liquid or gel composition is for cosmetic treatment.

In accordance with an embodiment of the method for percutaneous administration of a liquid or gel composition of the invention, a needle device or an injection apparatus is used.

Further objects and advantages of the present invention will be discussed below by means of exemplifying embodiments. These and other features, aspects and advantages of the invention will be more fully understood when considered with respect to the following detailed description, appended claims and accompanying drawings.

BRIEF DESCRIPTION OF THE DRAWINGS

The invention will now be described in more detail and with reference to the appended drawings in which.

DESCRIPTION OF PREFERRED EMBODIMENTS

In this description as well as the claims, a proximal end, or similar, is to be understood as the part of a component which, when the needle device or injection apparatus is in use, will be closer to the injection site, i.e. the skin of a patient. A distal end, or similar, on the other hand, should be understood as the part of a component which, when the needle device or injection apparatus is in use, will be further away from the injection site.

Figure 1:
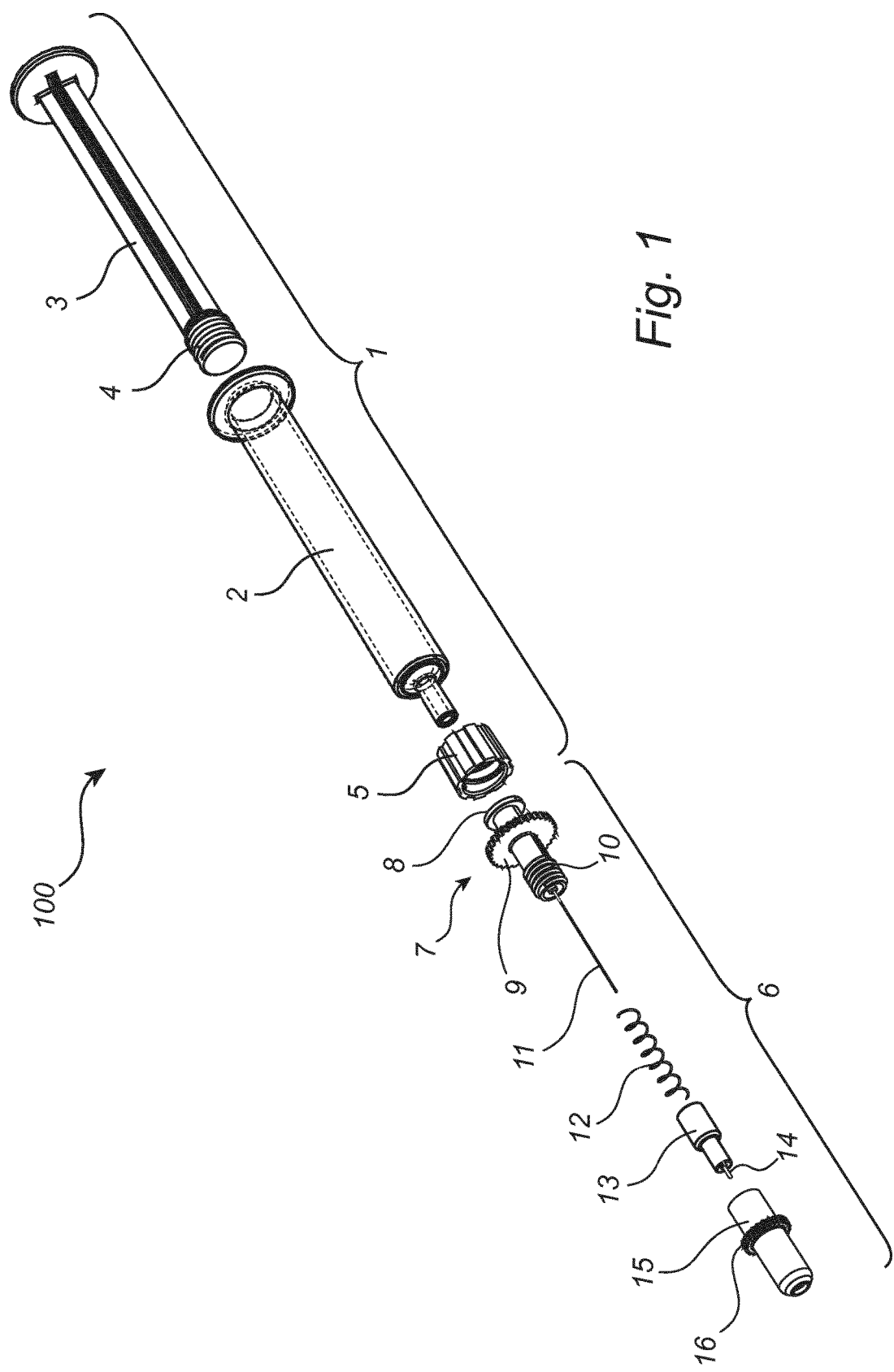
FIG. 1 is an exploded schematic perspective view of a first embodiment of the injection apparatus according to the invention.
Figure 2:
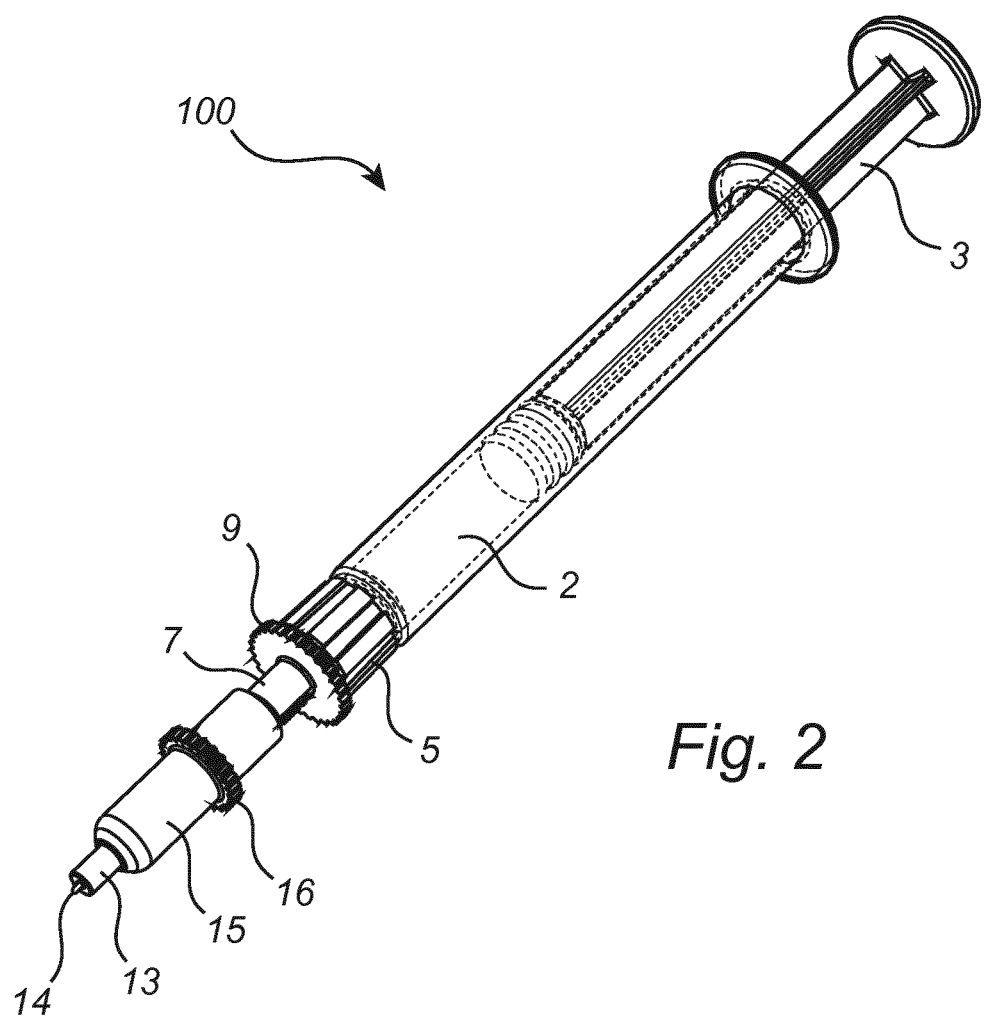
FIG. 2 is a schematic perspective view of a first embodiment of the injection apparatus according to the invention.
Figure 3:
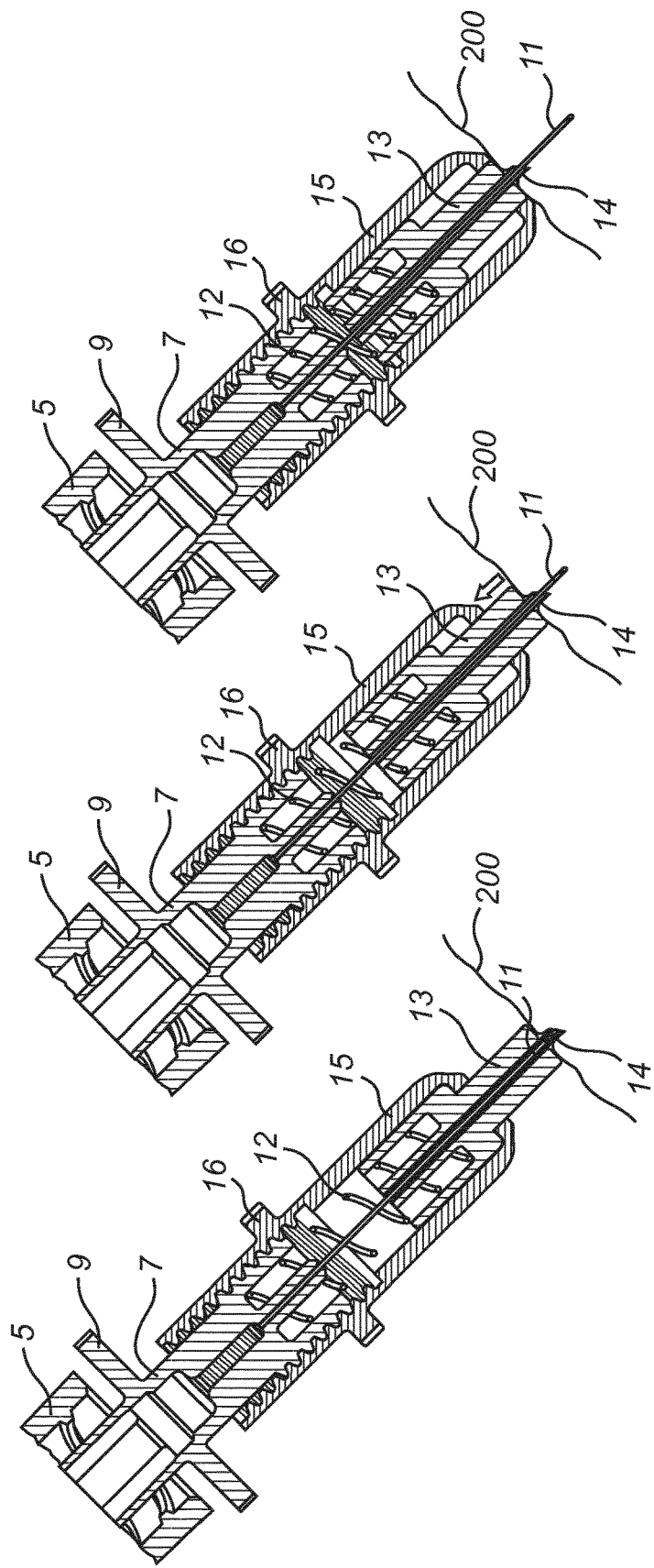
FIGS. 3a-3c show schematic cross-sectional side views of different stages of operation of an injection apparatus according to the invention.

A first embodiment of the injection apparatus 100 according to the invention is shown in FIGS. 1 and 2 where FIG. 1 shows an exploded view where each separate component and its position relative to the other components can be seen and FIG. 2 shows the injection apparatus 100 in an assembled state. The injection apparatus 100 comprises an injector in the form of a syringe 1 comprising a barrel 2, a plunger rod 3, a plunger 4 and a locking device 5. In this embodiment the locking device comprises a male Luer Lock connection fitting. Of course, many other locking devices are conceivable, such as Luer or other press-fit connections, threaded connections and others, all obvious to the skilled person. Coupled to the injector 1 is a needle device 6. The needle device 6 in its turn comprises an adaptor 7 having a female Luer Lock connection fitting 8 which fits into the male fitting 5 of the syringe 1 such that the syringe 1 and the needle device 6 can be connected to each other. The adaptor 7 further comprises an adjusting collar 9, the function of which will be described later on, and a threaded part 10. A cannula 11 having a blunt proximal end is fitted to the adaptor 7. The cannula 11 comprises a lateral orifice, not shown in the figures, near the blunt end thereof through which orifice a liquid or gel composition can be expelled. The lateral orifice has a smooth design which avoids damage to the tissue and allows the liquid or gel composition to flow easily through and out of the cannula. A second housing element 15 is connected to the adaptor 7 by means of an internal thread at a distal end of said second housing element 15 and an external thread 10 provided at a proximal end of the adaptor 7. An adjusting collar 16 is provided on the second housing element 15 with which the adjustment of the relative position between the second housing element 15 and the adaptor 7 is simplified. Fitted within said second housing element 15 is a first housing element 13 and the first and the second housing elements 13, 15 are moveable relative to each other between a compressed and an extended position, this will be described thoroughly with respect to FIGS. 3a-3b. A resilient member in the form of a spring 12 is provided between the adaptor 7 and the first housing element 13 biasing the housing elements 13, 15 towards their extended position. A cutting element 14 is provided at a proximal end of the first housing element.

Referring now to FIGS. 3a-3b as well as to previously described FIGS. 1 and 2, the functioning of an injection apparatus 100 when used for e.g. cosmetic treatment will be described. A user, such as a doctor, a nurse or any other person capable of performing the cosmetic treatment positions the injection apparatus 100 near a skin region 200 to be treated. Then the user, holding the injector 1, penetrates the upper skin layer, the epidermis, of the skin region to be treated 200 by pushing the cutting element 14 towards the skin. The cutting element 14 is disclosed in this embodiment in the form of a beveled needle mounted within the proximal opening in the first housing element 13. Another solution for the cutting element 14 will described later on with reference to FIG. 5. The axial position of the beveled needle within the first housing element 13 will vary depending on the intended cutting depth. It is also possible to reduce the risk of coring by arranging the beveled needle at such a position in the opening of the first housing element 13 that a part of the cutting edge of the beveled needle is hidden within the opening in the first housing element 13. The actual cutting edge of the cutting element 14 will then only extend around a part of the perimeter of the opening in the first housing element 13, thus reducing the risk for coring of skin tissue to occur. Spring 12 has a spring rate stiff enough to ensure that the cutting element 14 creates an opening in the skin before the spring yields. This first stage can be seen in FIG. 3a. As the user continues to push, see FIG. 3b, the spring will yield and the first and second housing elements 13, 15 will start to move relative to each other towards a compressed position. As this takes place, cannula 11 will move relative to cutting element 14 and eventually the cannula 11 will extend beyond cutting element 14 and penetrate deeper into the skin of the patient. This relative movement occurs since the cannula 11 is fixedly mounted to the adaptor 7 which in turn is mounted to the second housing 15. A continued pushing of the user will move the syringe 1, adaptor 7, cannula 11 and second housing element 15 closer to the skin region 200 of the patient while first housing element 13 and cutting element 14 remains stationary relative to the skin region 200. When the position shown in FIG. 3c is reached, no further relative movement between the first and second housing element can take place. This since a proximal end of the second housing element 15 has reached the surface of skin region 200. At this point, cannula 11 has reached its injection depth and the user manipulates the injector in order to expel a suitable amount of liquid or gel composition into the tissue surrounding the cannula 11. The spring rate of the helical spring 12 is preferably chosen to be stiff enough such that the cutting element 14 can penetrate the skin of the patient without any relative movement between the first and the second housing element taking place. It should however not be so stiff that an unnecessary high force has to be used in order to initiate the relative movement between the first and second housing element and thereby the introduction of the cannula 11 into the tissue of the patient. This since an unnecessary high spring rate can be uncomfortable for the patient. The force necessary to penetrate the epidermis of the skin with the cutting element 14 depends on the size and the shape of the cutting element and can vary from a few tenths of a Newton when using a very small and sharp micro needle as cutting element 14 up to 2-4 Newton when a beveled needle is used as cutting element 14. The spring rate of the helical spring 12 should therefore be chosen considering the properties of the cutting element 14 and probably also the properties of the skin region 200 to be treated since the properties of different skin regions differs from each other. The spring rate of the spring 12 should be chosen such that at least the force necessary to penetrate the epidermis is required to compress the spring to avoid that the blunt cannula 11 extends beyond the cutting element 14 at a too early stage. That would result in the blunt end of the cannula taking the lead during penetration of the epidermis which can be perceived as a discomfort to the patient since a rather high force will be necessary.

The main advantage with the injection apparatus according to the present invention is that bruising of the skin and tissue trauma can be avoided. This is due to the collaboration between the sharp cutting element 14 and the blunt cannula. The cutting element 14 is designed to cut through the tissue epidermis but not into the subjacent dermis. Since the epidermis does not contain any blood vessels and the cutting element does not reach below the epidermis, bruising is very unlikely to occur due to the cutting element. The length of the cutting element 14 should be chosen such that the cutting element 14 creates an opening through the epidermis but does not penetrate into the subjacent dermis in order to avoid rupturing of blood vessels therein. Of course, it would also be possible to provide a needle device 6 having an adjustable cutting element 14. Alternatively, needle devices 6 having cutting elements with different lengths can be provided for different skin regions. In a following step, when an opening in the epidermis has been created, the blunt cannula is inserted into the dermis, and possibly also into the hypodermis, or subcutis, where the liquid or gel composition is injected. Examples of compositions that can by injected with the injection apparatus of the present invention is gels of hyaluronic acid, such as Restylane Vital™ or Restylane Vital Light™. The blunt cannula does not perform any cutting action as it penetrates the tissue. Instead, the tissue of the layers beneath the epidermis is pushed aside by the blunt proximal end of the cannula 11 and the blood vessels can remain intact thus preventing bruising and tissue trauma. The final depth of the cannula 11 can be adjusted by means of the threaded connection 10 between the adaptor 7 and the second housing element 15, the adjusting collars 9, 16 are convenient to use for this purpose. The further into the second housing element 15 the adaptor 7 is screwed, the deeper the cannula 11 will reach into the tissue of the patient. With the needle device 6 of the present invention, it is thus possible to finely adjust the depth where injection takes place. And since the injection apparatus of the present invention will come to a stop when the proximal surface of the second housing element 15 reaches the skin of the patient, it is very easy for a user to repeatedly perform injection at exactly the same depth. All that has to be done is pushing the injector 1 with the needle device 6 against the skin of the patient until the second housing element 15 reaches the skin of the patient and thereafter actuate the injector in order to inject a suitable amount of liquid or gel composition. The handling will be even easier for a user if the injector comprises an automatic or semi-automatic injector, for example electronic injectors or spring loaded injectors, which are capable of expelling any desired amount of liquid or gel composition with a high accuracy and repeatability. Another advantage with the present invention is the fact that a user does not have to keep track of the location of the opening in the dermis. In prior art injection methods, where the opening in the skin is created in a first stage using a first instrument which is then put aside and the blunt cannula is inserted in a second stage it can sometimes actually be hard to retrieve the opening again. With the present invention, the creation of the opening and the insertion of the blunt cannula into the tissue takes place in one continuous motion and since the cutting element 14 remains in its epidermis penetrating position and acts as a guiding element for the blunt cannula 11 towards the opening created by the cutting element 14. When it comes to the diameters of the cutting element 14 and the cannula 11, these varies with the intended use. Concerning the cannula 11, common sizes are 21 G-30 G. Since the cutting element in the embodiment described in FIGS. 1-4 comprises a beveled needle through which the cannula shall pass, the size of the needle has to be chosen to allow this. This would correspond to needle sizes of 18 G-23 G for regular-wall needles. For needles having thicker or thinner walls, the sizing is adapted correspondingly. However, cannulas and needles of other sizes are also possible, for example 31 G and 32 G cannulas are very well imaginable for the needle device according to the present invention.

The needle device of the present invention is especially convenient when performing cosmetic treatment of e.g. the face where bruising is particularly inconvenient. Cosmetic treatment such as skin boosting requires regular treatment, typically at three occasions initially with one week between each treatment. Thereafter, re-treatment is necessary once or twice every year. The traditional method using a hypodermic needle will probably not cause post-treatment bruising at each injection site but since each treatment includes a high number of injections, it is very likely that bruising will occur to some extent. With the present invention on the other hand, bruising and tissue trauma can be avoided.

Figure 4:
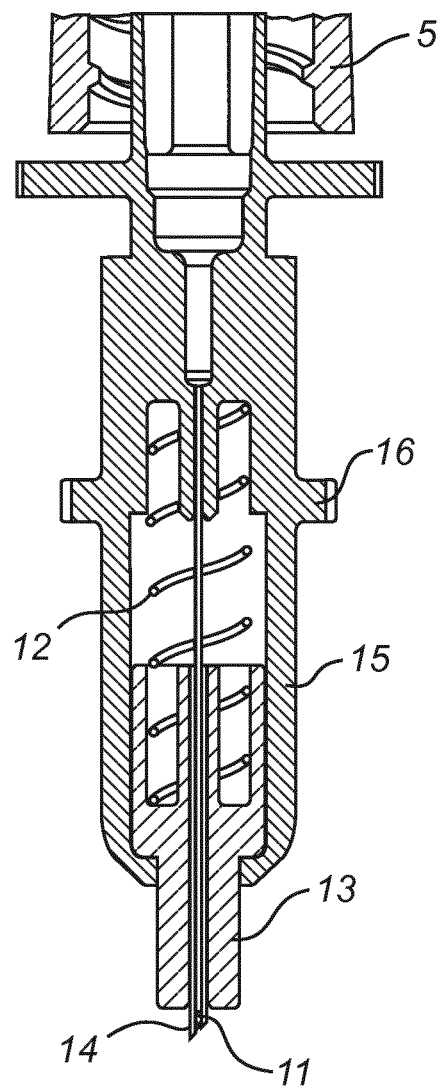
FIG. 4 shows a schematic cross-sectional side view of a second embodiment of the injection apparatus according to the invention.

FIG. 4 shows in a schematic way an alternative embodiment of the needle device of the present invention. In this embodiment, the adaptor has been omitted and the second housing element 15 of the needle device 6 is mounted directly to the locking device 5. This means that the length with which the cannula 11 extends beyond the cutting element 14 cannot be adjusted but for most applications a fixed length will be sufficient. In order to assemble the needle device of this embodiment, the second housing element 15 could be made to comprise two half-shells which are interconnectable. Other assembly solutions are also conceivable to the skilled person.

Figure 5:
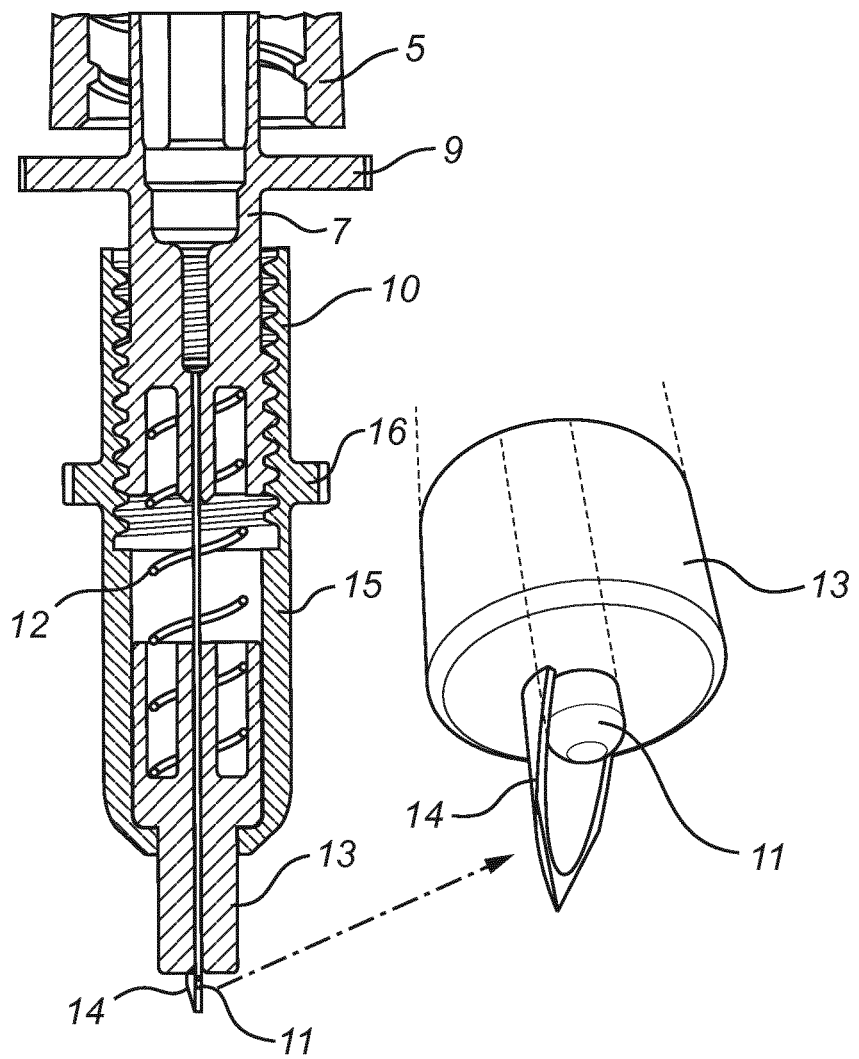
FIG. 5 shows a schematic cross-sectional side view of a third embodiment of the injection apparatus according to the invention as well as an enlargement of the proximal end thereof.

FIG. 5 shows in a schematic way a second alternative embodiment of the needle device of the present invention. In this embodiment, the cutting element 14 does not comprise a beveled needle. Instead, a jag is arranged near the opening in the first housing element. This is perfectly sufficient to create an opening in epidermis and if the jag is made up from a micro needle it can be made extremely sharp resulting in fine incisions which heal good, leaving no or at least almost no scar tissue. The sharpness of such jags further reduces the force necessary to penetrate epidermis which facilitate handling and reduces discomfort of the patient.

Finally, it is realized, that even though injectors in the form of traditional syringes have been disclosed in this application it should be noted that a many other types of injectors could be used without deviating from the scope of the application as defined by the appended claims. For example syringes for use with exchangeable cartridges containing liquid or gel compositions could be used. Further, re-chargeable electronic injectors for use with exchangeable cartridges containing liquid or gel compositions would also be suitable as well as injectors having other means than batteries for accumulating energy such as wounded springs or pneumatic injectors. Further, instead of using a helical spring as a resilient element within the housing, many alternative solutions are possible as well, such as elastomeric elements or air springs. The injection of crosslinked or non-crosslinked hyaluronic acid gels has been mentioned as a possible area of use for the device according to the invention. The hyaluronic acid gel is useful as a medical device, e.g. a dermal filler, for cosmetic use. It may also be useful in medical surgery, e.g. in eye surgery, joint surgery and medical cosmetic surgery or as a medicament, e.g. for treatment of joint disease. Naturally, it is possible to use the device according to the present invention with other liquid compositions, and preferably gel compositions, such as hydrogels. The device is also useful for injecting other types of dermal fillers than hyaluronic acid, e.g. collagen, calcium hydroxyl apatite, poly-L-lactic acid (PLLA), polymethylmethacrylate (PMMA), polycaprolactone and polyacrylamide. Furthermore, the device is useful for injecting liquid compositions comprising active substances, e.g. bioactive agents, local anesthetics, cicatrizants, antioxidants or botulinum toxin. A preferred liquid composition of this type is a gel composition with a hyaluronic acid gel carrier and an active substance, e.g. a local anesthetic or a cictrizant, such as dextranomer beads.

The invention claimed is:

1. A needle device configured for an injection apparatus, wherein said needle device comprises:
   a housing configured to be mounted to an injector, said housing comprising a first housing element provided towards a proximal end of said needle device and a second housing element provided towards a distal end of said needle device;
   a cutting element arranged at a proximal end of said first housing element, said cutting element having a sharp proximal end;
   a cannula fitted to the second housing element, said cannula having a blunt proximal end; and
   an opening for said cannula provided at the proximal end of the first housing element,
   wherein the first housing element and the second housing element are moveable relative to each other between an extended position and a compressed position,
   wherein the proximal end of the cannula does not extend beyond the proximal end of the cutting element when the first and second housing elements are in the extended position,
   wherein the cannula extends through the opening of the first housing element and past the proximal end of the cutting element when the first and second housing elements are in the compressed position, and
   wherein the first housing element is provided within the second housing element, and a resilient member is provided within the housing and biases the first housing element and the second housing element in a direction from the compressed position towards the extended position.

2. The needle device configured for an injection apparatus according to claim 1, wherein the second housing element comprises an adaptor arranged to mount the needle device to the injector and wherein said cannula is fitted to said adaptor and said adaptor is adjustably mounted to the second housing element, the needle device thereby being configured to regulate how far beyond the proximal end of the cutting element the cannula extends when the first housing element and second housing element is in the compressed position.

3. The needle device configured for an injection apparatus according to claim 2, wherein the adaptor is mounted to the second housing element by a threaded connection.

4. The needle device configured for an injection apparatus according to claim 1, wherein the cutting element comprises a beveled needle provided with a sharp tip, wherein the cannula and the beveled needle are coaxially mounted such that the cannula extends through an interior of the beveled needle when the first housing element and the second housing element is in the compressed position.

5. The needle device configured for an injection apparatus according to claim 1, wherein the cutting element extends partly around a perimeter of the opening in the first housing element.

6. The needle device configured for an injection apparatus according to claim 1, wherein the cutting element comprises a micro needle.

7. The needle device configured for an injection apparatus according to claim 1, wherein the cannula having the blunt proximal end comprises a lateral orifice through which a liquid composition can be delivered.

8. The needle device configured for an injection apparatus according to claim 1, wherein the cutting element has a length between 0.05 mm to 1.5 mm.

9. An injection apparatus comprising an injector and a needle device according to claim 1.

10. The injection apparatus according to claim 9, wherein the injector comprises a container filled with a liquid or gel composition for cosmetic treatment.

11. A method for percutaneous administration of a liquid or gel composition, the method comprising mounting a needle device according to claim 1 to the injector, the injector comprising a container filled with a liquid or gel composition to form an injection apparatus; and performing percutaneous administration of the liquid or gel composition with the injection apparatus.

12. The method according to claim 11, wherein the liquid or gel composition is for cosmetic treatment.

13. A method for percutaneous administration of a liquid or gel composition, comprising the following steps:
   penetrating the epidermis at a desirable skin region by pressing a cutting element having a sharp proximal end against the skin to create an opening in the epidermis, at a first position of the cutting element and a cannula relative to the epidermis;
   inserting the cannula having a blunt proximal end through the opening created in the epidermis by moving the cannula relative to the cutting element, while maintaining the cutting element in an epidermis penetrating position, wherein the proximal end of the cannula is inserted to a greater depth in the skin than the proximal end of the cutting element;
   said penetrating and inserting steps being performable in one continuous motion;
   administrating the liquid or gel composition through the cannula;
   withdrawing the cannula and the cutting element in one motion; and
   repeating the penetrating, inserting, administrating and withdrawing steps at a second position of the cutting element and the cannula relative to the epidermis, the second position being different from the first position,
   wherein the penetrating, inserting, administrating and withdrawing steps are performed using a needle device configured for an injection apparatus, wherein said needle device comprises:
   a housing configured to be mounted to an injector, said housing comprising a first housing element provided towards a proximal end of said needle device and a second housing element provided towards a distal end of said needle device;
   the cutting element arranged at a proximal end of said first housing element, said cutting element having the sharp proximal end;
   the cannula fitted to the second housing element, said cannula having the blunt proximal end; and
   an opening for said cannula provided at the proximal end of the first housing element,
   wherein the first housing element and the second housing element are moveable relative to each other between an extended position and a compressed position,
   wherein the proximal end of the cannula does not extend beyond the proximal end of the cutting element when the first and second housing elements are in the extended position, wherein the cannula extends through the opening of the first housing element and past the proximal end of the cutting element when the first and second housing elements are in the compressed position, and wherein the first housing element is provided within the second housing element, and a resilient member is provided within the housing and biases the first housing element and the second housing element in a direction from the compressed position towards the extended position.

14. The method for percutaneous administration of a liquid or gel composition according to claim 13, wherein the liquid or gel composition is for cosmetic treatment.

\* \* \* \* \*